US007186795B2

(12) United States Patent
Kim et al.

(10) Patent No.: US 7,186,795 B2
(45) Date of Patent: Mar. 6, 2007

(54) LACTOFERRICIN GENE AND TRANSFORMANT EXPRESSING LACTOFERRICIN

(75) Inventors: Ha-Kun Kim, Taejon (KR); Dae-Kyung Kang, Suwon-si (KR); Ju-Hoon Lee, Cheonan-si (KR)

(73) Assignee: Easy Bio System, Inc., Seoul (KR)

( * ) Notice: Subject to any disclaimer, the term of this patent is extended or adjusted under 35 U.S.C. 154(b) by 296 days.

(21) Appl. No.: 10/496,806

(22) PCT Filed: Nov. 30, 2002

(86) PCT No.: PCT/KR02/02253

§ 371 (c)(1),
(2), (4) Date: May 27, 2004

(87) PCT Pub. No.: WO03/046002

PCT Pub. Date: Jun. 5, 2003

(65) Prior Publication Data

US 2006/0148029 A1    Jul. 6, 2006

(30) Foreign Application Priority Data

Nov. 30, 2001  (KR) ............ 10-2001-0075437

(51) Int. Cl.
*A61K 38/00*   (2006.01)
*C12N 15/00*   (2006.01)
*C12P 21/06*   (2006.01)
*C07H 21/02*   (2006.01)
*C07H 21/04*   (2006.01)

(52) U.S. Cl. .......... 530/300; 435/440; 435/69.1; 435/320.1; 435/252.3; 536/23.1; 536/23.5; 536/23.4

(58) Field of Classification Search ............ 530/300; 536/23.1, 23.5, 23.4; 435/440, 69.1, 320.1, 435/252, 252.3
See application file for complete search history.

(56) References Cited

U.S. PATENT DOCUMENTS 5,317,084 A    5/1994 Tomita et al.
6,183,992 B1 *  2/2001 Kim et al. .......... 435/69.7

FOREIGN PATENT DOCUMENTS

WO    WO 98/06860 A1 *  2/1998
WO    WO 00/12542 A2    3/2000

OTHER PUBLICATIONS

Vernooij et al. "Plant optimized Lactoferricin B constructing oligo 2", SEQ ID No. 3, alignment result 4, Database: N_Geneseq_21, Accession No. AAV28423, Feb. 19, 1998.*

OTHER PUBLICATIONS

Genbank Accession No. 1LFL, 'Bovine lactoferricin(Lfeinb), Nmr, 20 Structures, Jun. 24, 1998.
Miyauchi et al., In: Cellular Immunology, 1998, vol. 187, pp. 34-37.

* cited by examiner

*Primary Examiner*—Jon Weber
*Assistant Examiner*—Rita Mitra
(74) *Attorney, Agent, or Firm*—Birch, Stewart, Kolasch & Birch, LLP

(57) ABSTRACT

Disclosed is a gene encoding a mutated lactoferricin peptide and an *E. coli* cell transformed with the same, wherein the mutated lactoferricin peptide has substitutions at the 7th and 10th amino acid residues of the wildtype bovine lactoferricin. The gene of the present invention can be expressed in *E. coli* at high efficiency, and the expressed mutated lactoferricin peptide can be purified at high yield, thus making its mass production possible.

6 Claims, 8 Drawing Sheets

BbsI site in Multiple cloning site
CC CGG GGA TCC GGA TGC GAA GAC GGC CCC
      BamHI                     BbsI GGG TCT TCT AGA GTC GAC CTG CAG GCA
    XbaI     SalI

FIG. 4

```
mag-1                    mag-F
───▶                     ───▶
AAAGAAGACGG CCC CTG TGC GAC GCT GAA GCT GTT GGT CCG GAA GCT TTC GCT GAC GAA
             P   L   C   D   A   E   A   V   G   P   E   A   F   A   D   E Lfc-3                    mag-2
   ───▶                     ◀───
GAC CTG GAC GAA TGC CCC CTG ATG TTC AAA TGC CGT CGT TGG GAA TGG CGT GTT
 D   L   D   E   C   P   L   M   F   K   C   R   R   W   E   W   R   V
            ◀───            ───▶
            mag-R           Lfc-F Lfc-R
                                                                ◀───
AAA AAA CTG GGT GCT CCG TCC ATC ACC TGC GTT CGT CGT GCT TTC ATG
 K   K   L   G   A   P   S   I   T   C   V   R   R   A   F   M Lfc-4
      ◀───
CCCCGGGTCTTCTAG..........
```

LACTOFERRICIN GENE AND TRANSFORMANT EXPRESSING LACTOFERRICIN

This is the U.S. National Phase of PCT Application No. PCT/KR02/02253 filed on Nov. 30, 2002. This application also claims priority to Patent Application No.10-2001-0075437 filed in Korea on Nov. 30, 2001. Priority is claimed under 35 U.S.C. § 119 § and 120 and the entire contents of the above applications are hereby incorporated by reference.

TECHNICAL FIELD

The present invention relates to a gene encoding a mutated lactoferricin peptide and an *E. coli* cell transformed with the same, and more particularly, to a gene encoding a mutated lactoferricin peptide having two substitutions, namely at the 7th and 10th amino acid residues of the wildtype bovine lactoferricin, a recombinant expression vector containing the gene, and an *E. coli* cell transformed with the recombinant expression vector.

PRIOR ART

Lactoferrin is a glycoprotein having a molecular weight of 80 kDa in milk and other body fluids, and plays an important role in the host defense system (Oram, et al., Biochim. Biophys. Acta 170:351–365, 1968). Lactoferricin, as a peptide generated by hydrolysis of lactoferrin by the proteinase pepsin, has higher antimicrobial activity than lactoferrin (Tomita, M. J. Dairy Sci. 74:4137–4142, 1991).

Bovine lactoferricin (hereinafter, referred to as "LfcB") originates from a peptide ranging from Phe17 to Phe41 at the N-terminus of bovine lactoferrin, and has a molecular weight of 3,124 Daltons. Lactoferricin is characterized as having potent antimicrobial activity against diverse microorganisms including bacteria and fungi. Especially, it was reported that lactoferrrincin has an effect of inhibiting the growth of *E. coli* 0157, *Helicobacter pylori* and *Candida albicans*, which are major objects of clinical studies (Yamaguchi, et al., Infect. Immun. 61:719–728, 1993). In addition, lactoferricin inhibits cancer metastasis, LPS-induced IL-6 response in monocytic cells, and iron/ascorbate-induced lipid peroxidation (Yoo, et al., Jpn. J. Cancer Res. 88:184–190, 1997; Mattsby-Baltzer, et al., Pediatr. Res. 40:257–262, 1996; and Wakabayashi, et al., Biosci. Biotechnol. Biochem. 63:955–957, 1999).

Lactoferrin and lactoferricin having such beneficial activities can be mass produced in bacteria by genetic engineering techniques. For example, lactoferrin can be produced on a largescale using *Aspergillus awamori* as an expression system with which lactoferrin is expressed as a fusion peptide at the N-terminus of glucoamylase of *A. awamori* and lactoferrin gene of mouse. In such an expression system, lactoferrin is secreted to culture medium at an amount of about 12 mg/L medium, and the expressed lactoferrin can be purified using ion exchange resins (Ward, et al., Bio/Technology 13:498–503, 1995). In addition, Salmon, et al., reported another expression system using baculovirus with which human lactoferrin is produced in Sf9 cells at an amount of 10–15 mg/L medium (Salmon, et al., Protein Expression and Purification 9, 203–210, 1997).

However, lactoferricin is featured in terms of being a small-sized peptide containing many basic residues, such as lysine or arginine, and having antimicrobial activity. With such unfavorable features for directly expressing lactoferricin in microorganisms, there is still no report of successful expression of lactoferricin using genetic engineering techniques.

On the other hand, Korean Pat. Publication No. 2000-263583 discloses a method of large-scale production of an antimicrobial peptide in a recombinant microorganism, in which a basic antimicrobial peptide gene is linked to an acidic peptide gene, and the resulting fusion gene is expressed in a bacterial host cell, leading to neutralization of the basic property of the antimicrobial peptide, essential for its antimicrobial activity, by the co-expressed acidic peptide, and thus temporally inhibiting the antimicrobial activity of the antimicorbial peptide and preventing death of the host cell. However, when using the method, lactoferricin is not overexpressed in *E. coli*, and moreover, the expressed lactoferricin is not purified at high yield.

Taking the problems encountered in the prior art into consideration, the present inventors completed the present invention by chemically synthesizing a gene encoding a mutated lactoferricin peptide to allow large-scale expression of lactoferricin in *E. coli* and facilitate its purification, preparing an expression vector containing the gene, introducing the gene into *E. coli* cells and treating the resulting transformants with IPTG to induce effective expression of lactoferricin, and confirming high production level of lactoferricin in *E. coli*.

DISCLOSURE OF THE INVENTION

Leading to the present invention, the intensive and thorough research into expression of lactoferricin in *E. coli*, aiming to overcome the above-mentioned problems, resulted in the finding that high expression of lactoferricin is achieved by fusing a gene encoding a mutated lactoferricin peptide having amino acid substitutions at the 7th and 10th residues of the wildtype bovine lactoferricin to an acidic peptide magainin gene, inserting the resulting fusion gene into a protein expression plasmid, and expressing the resulting expression plasmid in *E. coli* by treating with IPTG to induce effective expression of lactoferricin, wherein the expressed lactoferricin is additionally purified at high yield.

It is therefore an object of the present invention to provide a mutated lactoferricin peptide having amino acid substitutions at the 7th and 10th residues of the wildtype bovine lactoferrin.

It is another object of the present invention to provide a gene encoding a mutated lactoferricin peptide.

It is still another object of the present invention to provide a recombinant expression vector pET-MLnX containing a fusion gene in which a gene encoding a mutated lactoferricin peptide is fused to a magainin gene.

It is a further object of the present invention to provide an *E. coli* cell transformed with a recombinant expression vector pET-MLnX.

It is a still further object of the present invention to provide a method of large-scale production of lactoferricin by culturing the above a transformed *E. coli* cell.

BRIEF DESCRIPTION OF THE DRAWINGS

The above and other objects, features and other advantages of the present invention will be more clearly understood from the following detailed description taken in conjunction with the accompanying drawings, in which:

FIG. 4 is a nucleotide sequence of a lactoferricin gene (SEQ ID NO: 20) in which primers used for preparation of a fusion gene of a magainin gene and a mutated lactoferricin gene are indicated;

BEST MODES FOR CARRYING OUT THE INVENTION

Figure 1:
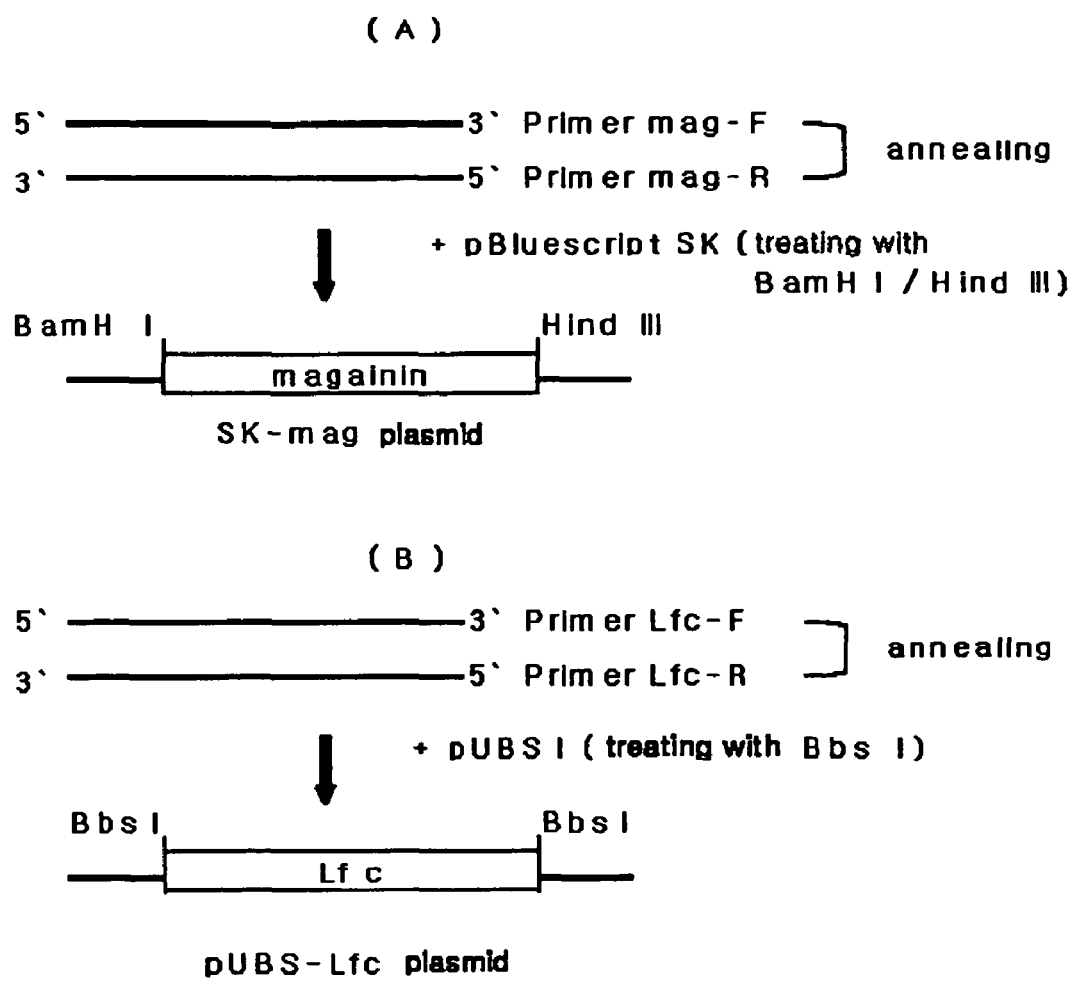
FIGS. 1A and 1B are schematic views showing processes of preparing a plasmid containing a magainin gene or a mutated lactoferricin gene, in which 1A shows a process of preparing a SK-mag plasmid containing a magainin gene and 1B shows a process of preparing a pUBS-Lfc plasmid containing a mutated lactoferricin gene.

The bovine lactoferrin-derived lactoferricin (LfcB), which has antimicrobial activity, is a peptide comprising 25 amino acids and having the amino acid sequence shown in SEQ ID NO: 1 (F-K-C-R-R-W-Q-W-R-M-K-K-L-G-A-P-S-I-T-C-V-R-R-A-F (Genebank Database Accession No. 3891493), and contains 7 basic lysine and arginine residues (Hoek, et al., Antimicrob. Agents Chemother. 41: 54–59, 1997). In accordance with the present invention, to effectively produce the basic residue-rich LfcB, a negatively charged peptide is used as a carrier, and thus allows a fusion peptide expressed in E. coli, comprising a lactoferricin peptide fused to the negatively charged peptide, to have a net neutral charge. The expressed fusion peptide is chemically cleaved using cyanogen bromide (CNBr) at a single methionine placed between the negatively charged peptide and the lactoferricin peptide, thus separating a lactoferricin peptide from the carrier peptide.

The 10th residue of the wildtype bovine lactoferricin is methionine. In this regard, to prevent internal cleavage of lactoferricin by CNBr, a lactoferricin gene having the 10th residue replaced by valine having a hydrophobic R group is prepared.

In addition, during research to improve purification yield of lactoferricin expressed in E. coli, the present inventors found that a lactoferricin peptide having glutamate substituted for Gln7 of the wildtype peptide is purified at a higher efficiency than the wildtype peptide.

Thus, in accordance with the present invention, there is provided a gene encoding a mutated lactoferricin peptide having glutamate and valine substituted for Gln7 and Met10 of the wildtype peptide, respectively. The mutated lactoferricin having two amino acid substitutions is fused to a carrier peptide having a net negative charge and overexpressed in E. coli, and then purified. The purified fusion peptide is chemically cleaved with CNBr to generate two separate pepetides, a lactopericcin peptide and a carrier peptide, and the separated lactoferricin peptide is purified through a QAE-Sephadex ion exchange resin.

In addition, IPTG is used to induce expression of the fusion peptide. IPTG is preferably added at an amount of 0.1–5 mM, and more preferably, 0.5–1 mM.

Biological activity of the mutated lactoferricin peptide obtained through the process as described above is evaluated by investigating its antimicrobial activity against E. coli. The mutated lactoferricin peptide produced using genetic engineering techniques is able to effectively inhibit the growth of E. coli at a concentration of more than 50 μg/ml, and such an antimicrobial activity of the mutated lactoferricin peptide is similar to that of a chemically synthesized wildtype lactoferricin peptide.

Therefore, a biologically active lactoferricin peptide is produced in E. coli according to the present invention, and the mutated lactoferricin peptide can be used instead of the conventional antibiotics, and as an immunomodulator and an antiviral agent.

The present invention will be explained in more detail with reference to the following examples in conjunction with the accompanying drawings. However, the following examples are provided only to illustrate the present invention, and the present invention is not limited to them.

EXAMPLE 1

Preparation of a Lactoferricin Expression Vector

A lactoferricin expression vector was prepared as follows. An nucleotide sequence (SEQ ID NO: 2) encoding a mutated lactoferricin peptide was prepared taking codons mainly used in gene expression in E. coli into consideration, not using the known nucleotide sequence of the wildtype bovine lactoferrin gene (Goodman, et al, Biochem. Biophys. Res. Commun. 180: 75–84, 1991).

To neutralize the basic proptery of lactoferricin, a gene encoding an acidic magainin peptide was used (Lee, et al., Protein Expression and Purification. 12: 53–60, 1998). The magainin gene was inserted into a plasmid, and the mutated lactoferricin gene according to the present invention was inserted into a plasmid. Thereafter, the two genes were fused by recombinational PCR using the two plasmids as templates.

Each of processes for preparing the above plasmids and fusion gene will be described in detail, below.

EXPERIMENTAL EXAMPLE 1

Preparation of a Plasmid Containing a Magainin Gene

In order to obtain a gene encoding a magainin peptide having many anionic amino acids (Lee, et al., Protein Expression and Purification. 12: 53–60, 1998) as a carrier for lactoferricin, two complementary oligonucleotides consisting of mag-F (SEQ ID NO: 6) and mag-R (SEQ ID NO: 7) were chemically synthesized, in which a BamHI site and a HindIII site were inserted into the 5' ends of mag-F and mag-R, respectively:

```
mag-F:
5'-GAT CGA CGC TGA AGC TGT TGG TCC      (SEQ ID NO: 6)
GGA AGC TTT CGC TGA CGA AGA CCT GGA
CGA A-3';
and mag-R:
5'-AGC TTT CGT CCA GGT CTT CGT CAG      (SEQ ID NO: 7)
CGA AAG CTT CCG GAC CAA CAG CTT CAG
CGT C-3'.
```

After the two oligonucleotides were chemically synthesized, their 5' ends were phosphorylated, and annealed. The resulting double stranded DNA was treated with BamHI and HindIII, and then cloned into a BamHI/HindIII-digested pBluescript SK(+) plasmid (Stratagene, USA), thus giving a SK-mag plasmid carrying a magainin gene (see, FIG. 1A).

EXPERIMENTAL EXAMPLE 2

Preparation of a Plasmid Containing a Lactoferricin Gene

In order to obtain a gene encoding a mutated lactoferricin peptide having amino acid substitutions at the 7th and 10th residues of the wildtype bovine peptide, two complementary oligonucleotides consisting of Lfc-F (SEQ ID NO: 8) and Lfc-R (SEQ ID NO: 9) were chemically synthesized by using the similar method as in Experimental Example 1, in which a sequence consisting of CCCC and a sequence consisting of GGGG were inserted into the 5' ends of Lfc-F and Lfc-R, respectively:

```
Lfc-F:
5'-CCC CTG ATG TTC AAA TGC CGT CGT      (SEQ ID NO: 8)
TGG GAA TGG CGT GTT AAA AAA CTG GGT
GCT CCG TCC ATC ACC TGC GTT CGT CGT
GCT TTC ATG-3';
and Lfc-R:
5'-GGG GCA TGA AAG CAC GAC GAA CGC      (SEQ ID NO: 9)
AGG TGA TGG ACG GAG CAC CCA GTT TTT
TAA CAC GCC ATT CCC AAC GAC GGC ATT
TGA ACA TCA-3'.
```

After the two oligonucleotides were chemically synthesized, their 5' ends were phosphorylated, and annealed. The resulting double stranded DNA was cloned into a BbsI-digested pUBSI plasmid (see, FIG. 3), thus giving a pUBS-Lfc plasmid carrying a lactoferricin gene (see, FIG. 1B).

Figure 2:
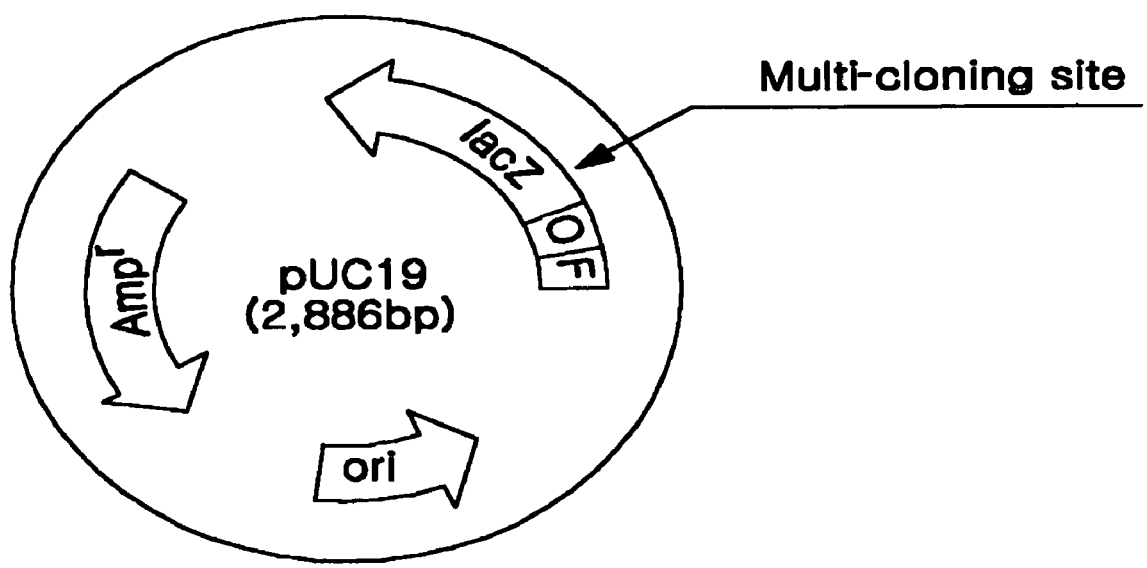
FIG. 2 is a schematic view showing a pUBSI plasmid produced by introduction of a BbsI site (SEQ ID NO: 19) to the multiple cloning site of pUC19 plasmid.

The plasmid pUBSI having a BbsI site was prepared by performing PCR using a pUC19 plasmid (Life Technology, USA) as a template and two primers, below, and transforming the resulting PCR product into XL1-Blue (Stratagene, USA) (see, FIG. 2):

```
BS-F:
5'-AGA CCC GGG GCC GTC TTC GCA TCC      (SEQ ID NO: 10)
GGA TCC CCG GGT ACC GAG CTC-3';
and BS-R:
5'-GGA TGC GAA GAC GGC CCC GGG TCT      (SEQ ID NO: 11)
TCT AGA GTC GAC CTG CAG GCA-3'.
```

EXPERIMENTAL EXAMPLE 3

Fusion of a Magainin Gene and a Lactoferricin Gene

Figure 3:
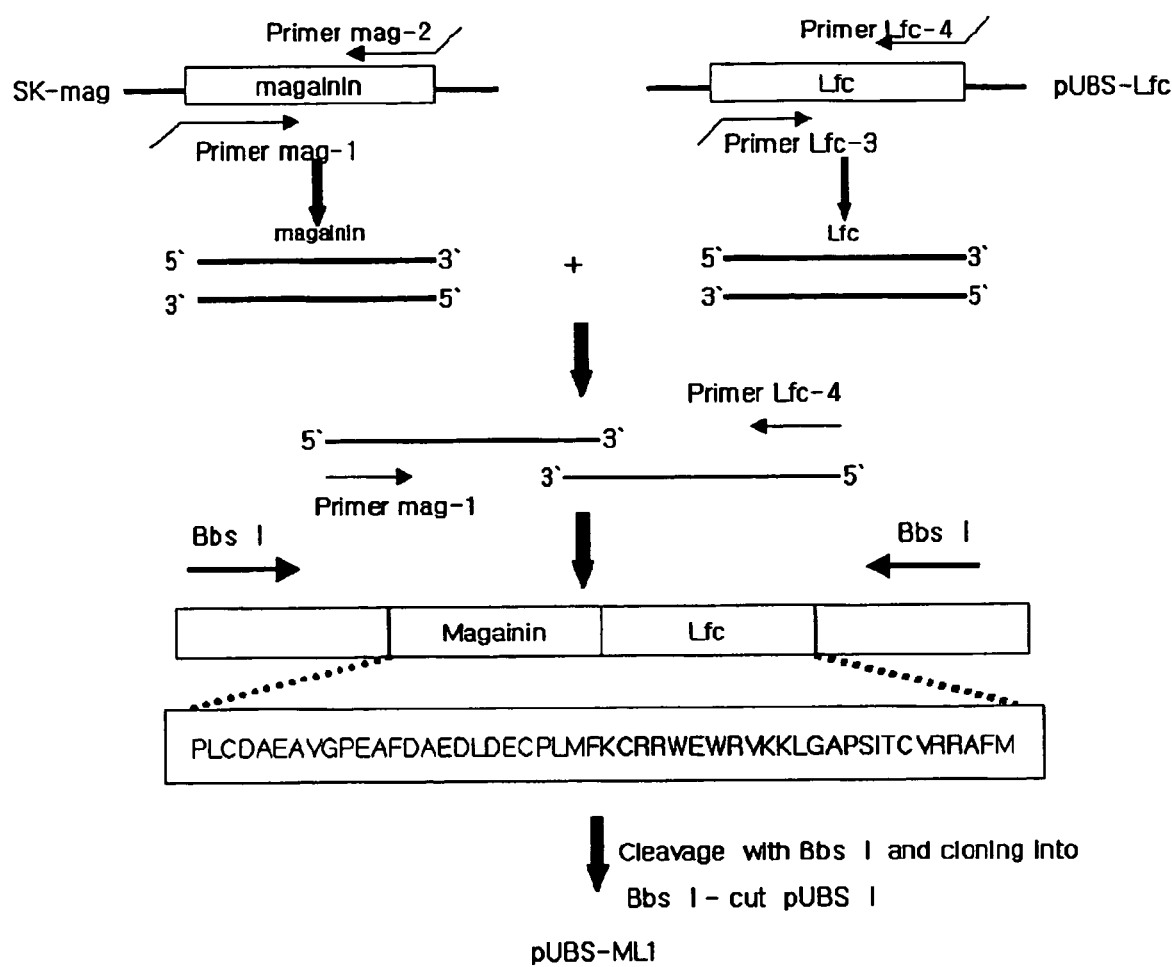
FIG. 3 is a flowchart showing a process of fusing a mutated lactoferricin gene to a magainin gene (SEQ ID NO: 5) by PCR.

A magainin gene and a lactoferricin gene were fused using a recombinantional PCR method, in which the plasmids SK-mag and pUBS-Lfc prepared in Experimental Examples 1 and 2, respectively, were used as templates (see, FIG. 3). First, to amplify a magainin gene, PCR was carried out using the SK-mag plasmid as a template and two primers: mag-1: 5'-AAA GAA GAC GGC CCC TGT GCG ACG CTG AAG CTG TTG GTC C-3' (SEQ ID NO: 12); and mag-2: 5'-CAT CAG GGG GCA TTC GTC CAG GTC TTC GTC AGC G-3' (SEQ ID NO: 13), thus generating a PCR product of 83 bp.

Separately, to amplify a lactoferricin gene, PCR was carried out using the pUBS-Lfc plasmid as a template and two primers: Lfc-3: 5'-CTG GAC GAA TGC CCC CTG ATG TTC AAA TGC CG-3' (SEQ ID NO: 14); and Lfc-4: 5'-CTA GAA GAC CCG GGG CAT GAA AGC ACG ACG AAC GCA GGT GAT GG-3' (SEQ ID NO: 15), thus generating a PCR product of 114 bp.

To link the magainin gene to the mutated lactoferricin gene, after mixing the amplified 83 bp magainin DNA fragment and the 114 bp lactoferricin DNA fragment at an equivalent ratio, a recombinational PCR was carried out using the mixture of DNA fragments and two oligonucleotide primers of mag-1 and Lfc-4, thus producing a magainin-lactoferricin gene of 176 bp (hereinafter, referred to as a "ML gene"). FIG. 4 shows the positions of the primers used for preparation of the fusion gene (SEQ ID NO: 4) consisting of a magainin gene and a lactoferricin gene on the nucleotide sequence of the fusion gene.

Since the oligonucleotides mag-1 and Lfc-4 each contain a BbsI site, the ML gene was digested with BbsI, and inserted into a BbsI-digested pUBSI plasmid, thus giving a pUBS-ML1 plasmid.

The plasmid pUBS-ML1 containing a ML gene was again digested with BbsI. The resulting 152 bp DNA fragment containing a ML gene was recovered, which contains a sequence consisting of CCCC at its 5' end and a sequence consisting of GGGG at its 3' end, followed by self-ligation, thus generating a (ML)n gene containing variable numbers of tandem repeats of the ML gene.

Copy number of the ML gene contained in the (ML)n gene carried by a pUBSI-ML1 plasmid was investigated by using a colony PCR method. The pUBSI-ML1 plasmid was introduced into XL1-Blue cells (Stratagene, USA) by electroporation. The resulting transformants were cultured on a solid medium. Then, a colony PCR was carried out, in which, since the plasmid pUBSI is derived from the plasmid pUC19, utilizing the M13 sequence in pUC19, a M13 forward sequencing primer: 5'-CCC AGT CAC GAC GTT GTA AAA CG-3' (SEQ D NO: 16); and a M13 reverse sequencing primer: 5'-AGC GGA TAA CAA TTT CAC ACA GG-3' (SEQ ID NO: 17) were used. As a result, the plasmid pUBSI-ML1 was found to comprise a tandem repeat of 1 to 6 copies of the ML genes.

EXPERIMENTAL EXAMPLE 4

Preparation of an Expression Vector of the Fusion Gene

Figure 5:
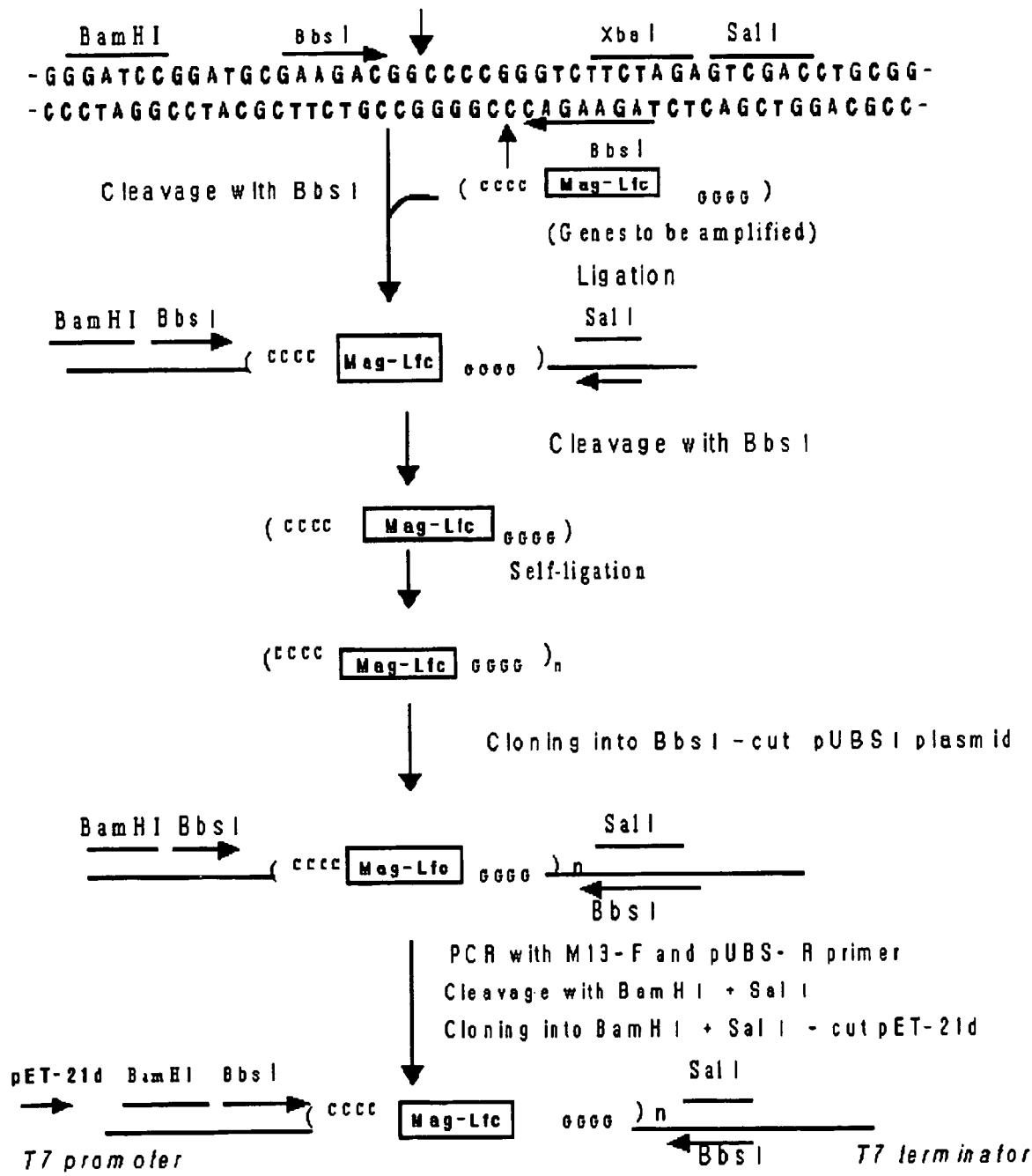
FIG. 5 is a flowchart showing a process of preparing a recombinant expression vector pET-MLnX expressing lactoferricin. SEQ ID NOS: 21 and 22 are shown at the top of the figure.

To form a continuous open reading frame of the ML gene with the sequence encoding $(His)_6$ in an expression vector pET-21d (Novagen, USA), the 3' end of the ML gene was modified by removing TGA from the XbaI site (TCTAGA), as follows. PCR was carried out using each of plasmids carrying a tandem repeat of 1 to 6 copies of the ML genes as a template, and the M13 forward sequencing primer of SEQ ID NO: 16 and a primer pUBS-R: 5'-CTG CAG GTC GAC TCT GAA GAC CC-3' (SEQ ID NO: 18). The resulting amplified DNA fragment was recovered and digested with BamHI and SalI, and then subcloned into a BamHI/SalI-digested pET21-d plasmid. As a result, pET-MLnX plasmids were prepared, which can express lactoferricin having glutamate and valine substituted for Gln7 for Met10, respectively, in E. coli (see, FIG. 5), wherein n is copy number of the ML gene. When containing one copy of the ML gene, the plasmid is designated pET-ML1X. Similarly, a pET-ML2X plasmid contains two copies of the ML gene, a pET-ML3X plasmid contains three copies of the ML gene, a pET-ML4X plasmid contains four copies of the ML gene, a pET-ML5X plasmid contains five copies of the ML gene, and a pET-ML6X plasmid contains six copies of the ML gene.

EXAMPLE 2

Expression and Purification of a Fusion Peptide

The pET-MLnX expression plasmids were introduced into E. coli BL21 (DE3) cells (Novagen, USA) by electroporation. The resulting transformants (E. coli BL21(DE3) [pET-MLnX]) were incubated in liquid media with agitation, in which 1 mM of IPTG was added to each of the media when OD600 reaches 0.5, thus inducing expression of a fusion peptide with a molecular weight of about 20 kDa. As a result, expression plasmids having 1 to 4 copies of the ML gene were found to effectively express a fusion peptide, while such an effective expression was not found by using the expression plasmids having 5 or more copies of the ML gene.

Figure 6:
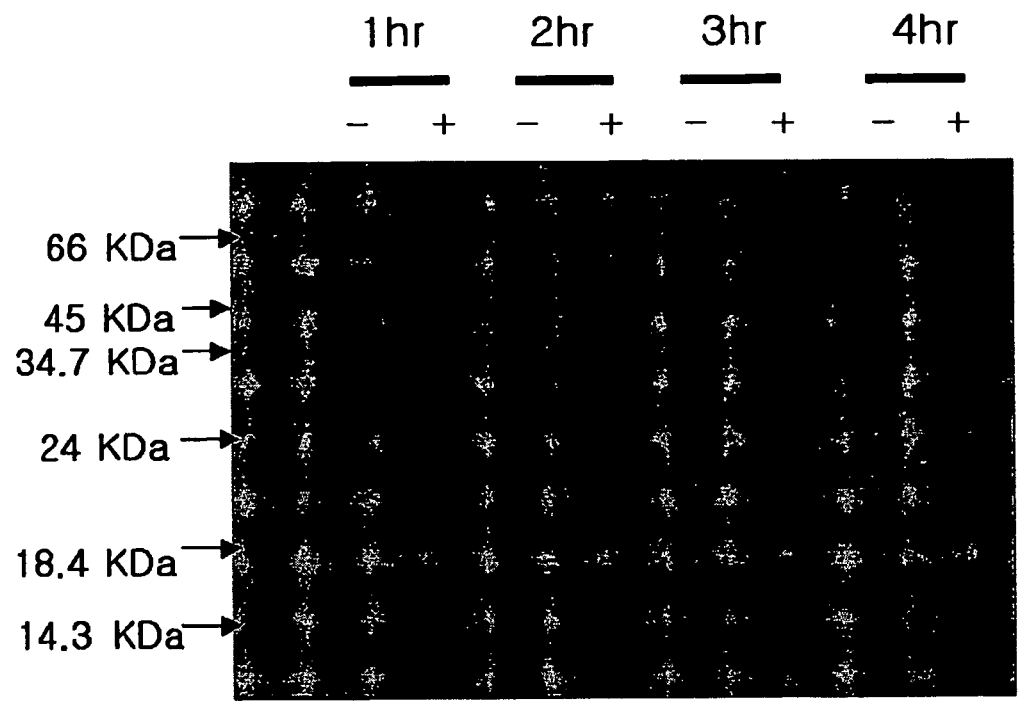
FIG. 6 is a photograph showing changes in the expression level of lactoferricin peptide by treatment with 1 mM IPTG according to time.

To obtain a high expression level of lactoferricin, a transformant E. coli BL21(DE3)[pET-ML4X], transformed with the expression plasmid pET-ML4X having a tandem repeat consisting of 4 copies of the ML gene, was incubated in LB liquid medium with agitation, and treated with 1 mM of IPTG when OD600 reaches 0.5 to induce expression of a fusion peptide with a molecular weight of 20 kDa. Expression levels of the fusion peptide were evaluated according to time. The maximum production of the fusion peptide was found at 3 hrs after treatment of IPTG (see, FIG. 6).

Figure 7:
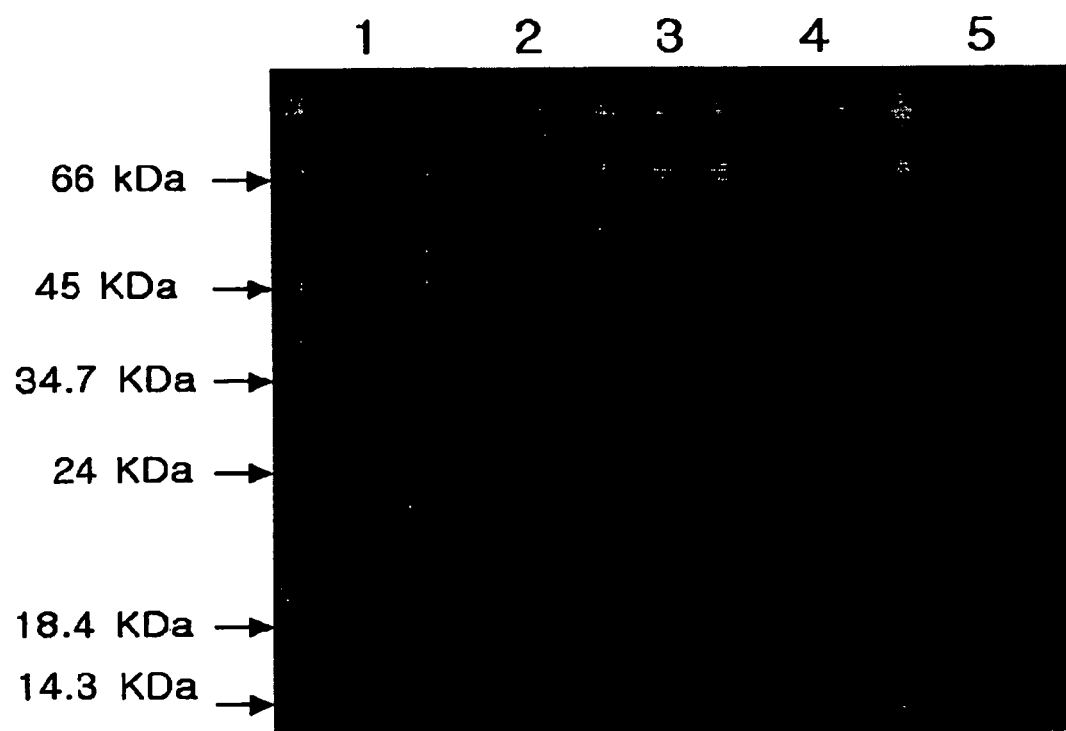
FIG. 7 is a photograph showing results of purification of a lactoferricin fusion peptide using a Ni-NTA resin, in which lane 1 is a sample of inclusion body dissolved in 8 M urea of pH 8.0, lane 2 is a sample passed through the Ni-NTA resin when the dissolved inclusion body of lane 1 is applied to the resin, lane 3 is a sample eluted from the resin by 8 M urea of pH 6.3, lane 4 is a sample eluted from the resin by 8 M urea of pH 5.9, and lane 5 is a sample eluted from the resin by 8 M urea of pH 4.6.
Figure 8:
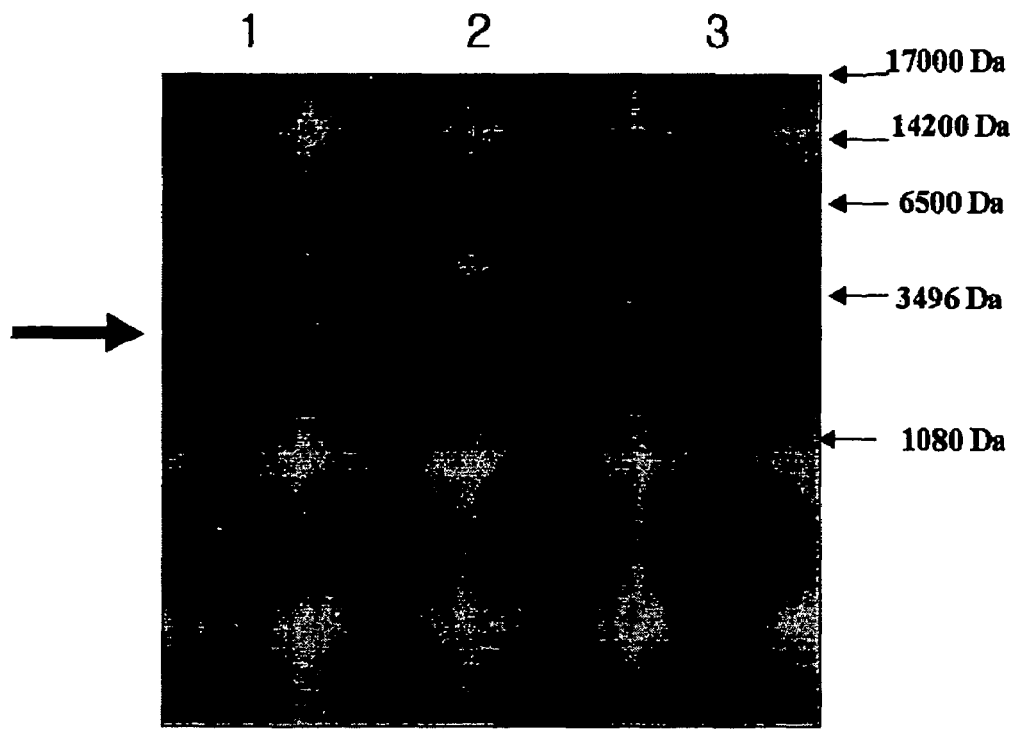
FIG. 8 is a photograph showing results of SDS-PAGE of samples obtained by purification of lactoferricin using an ion exchange resin, in which lane 1 is lactoferricin produced in E. coli, lane 2 is chemically synthesized lactoferricin, and lane 3 is a sample before application to ion exchange chromatography after treatment of a lactoferricin fusion peptide with CNBr.

Based on these results, the transformant was incubated in 5 L of LB liquid medium, and treated with 1 mM of IPTG to induce expression of the fusion peptide under the same condition as in the above small-scale production, followed by incubation for 3 more hrs. Bacterial cells were harvested, disrupted and centrifuged, thus generating a pellet. Inclusion body was recovered from the pellet. Thereafter, the recovered inclusion body was dissolved in 5 mL of 8 M urea of pH 8.0, and applied to a Ni-NTA resin. The Ni-NTA resin was washed with 8 M urea of pH 6.3 to remove impurities, and proteins bound to the resin were eluted with 8 M urea of pH 5.9, thus confirming production of a lactoferricin fusion peptide in the transformant (see, FIG. 7). In order to separate lactoferricin from the eluted fusion peptide, the fusion peptide dissolved in 8 M urea was dialyzed in distilled water using a dialysis bag, resulting in removal of urea. The fusion peptide, denatured by dialysis, was harvested by centrifugation. The recovered fusion peptide was dissolved in 2 ml of 70% formic acid, and treated with 0.5 g of CNBr to cleave the region between the carrier peptide magainin and lactoferricin. The resulting lactoferricin separated from the fusion peptide was purified by QAE-Sephadex chromatography, in which its purification yield was about 10 mg/L medium. As a result of SDS-PAGE, the purified lactoferricin expressed in E. coli was found to have the same molecular weight as the chemically synthesized wildtype lactoferricin (see, FIG. 8). In addition, an amino acid sequence of 5 residues at the N-terminus of the lactoferricin expressed in E. coli was determined using an Applied Biosystems Procise Sequencer, and found to have a sequence of Phe-Lys-Cys-Arg-Arg. Such an amino acid sequence at the N-terminus was found to be identical to that of the wildtype bovine lactoferricin. These results indicate that lactoferricin is successfully expressed in E. Coli and purified.

COMPARATIVE EXAMPLE

Figure 9:
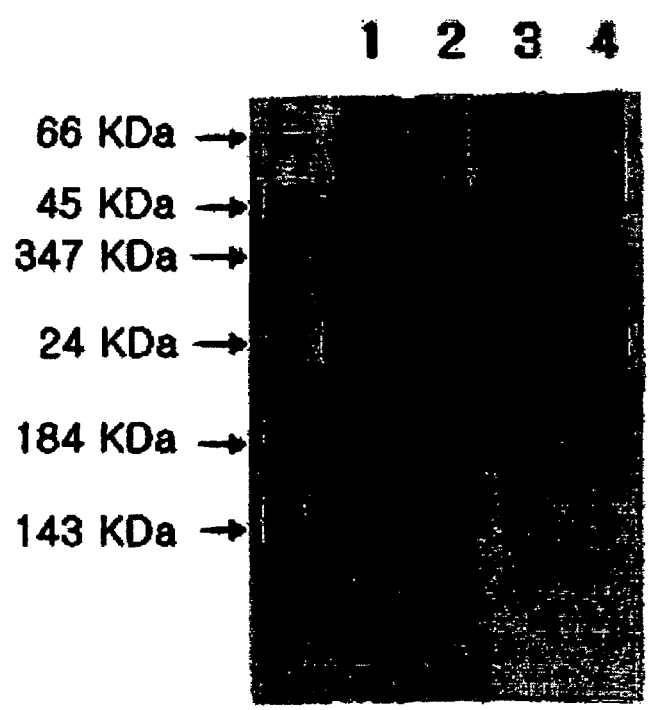
FIG. 9 is a photograph showing solubility of a lactoferricin fusion peptide expressed by a pET-ML4 plasmid carrying a gene encoding a mutated lactoferricin peptide without substitution of the 7th residue of the wildtype peptide, in which lane 1 is inclusion body dissolved in 8 M urea, lane 2 is a supernatant after centrifuging inclusion body dissolved in 8 M urea, lane 3 is inclusion body dissolved in 6 M GuHCl, and lane 4 is a supernatant after centrifuging inclusion body dissolved in 6 M GuHCl.

Purification Efficiency of Lactoferricin with No Substitution for the 7th Residue According to the same method as described above, except for no substitution of the 7th residue, a gene encoding a mutated lactoferricin peptide with no glutamate substituted for the 7th residue was prepared and expressed, and the mutated lactoferricin expressed in E. coli was purified. When expressing a pET-ML4 plasmid containing a mutated lactoferricin gene with no substitution of the 7th residue, inclusion body similar to that in Example 2 was formed. However, the inclusion body was not easily dissolved in 8 M urea or 6 M GuHCl. Thus, when purifying lactoferricin using a Ni-NTA resin, its purification yield was found to be reduced (see, FIG. 9). In SDS-PAGE, the lactoferricin peptides with or without substitution of the 7th residue were observed to migrate at different rates, and such a difference was believed to originate from their different net charges (see, FIGS. 7 and 9). These results indicate that when having glutamate substituted for the 7th residue, a lactoferricin peptide expressed in E. coli can be purified at a high efficiency.

EXAMPLE 3

Assay for Biological Activity of a Purified Lactoferricin Peptide

Figure 10:
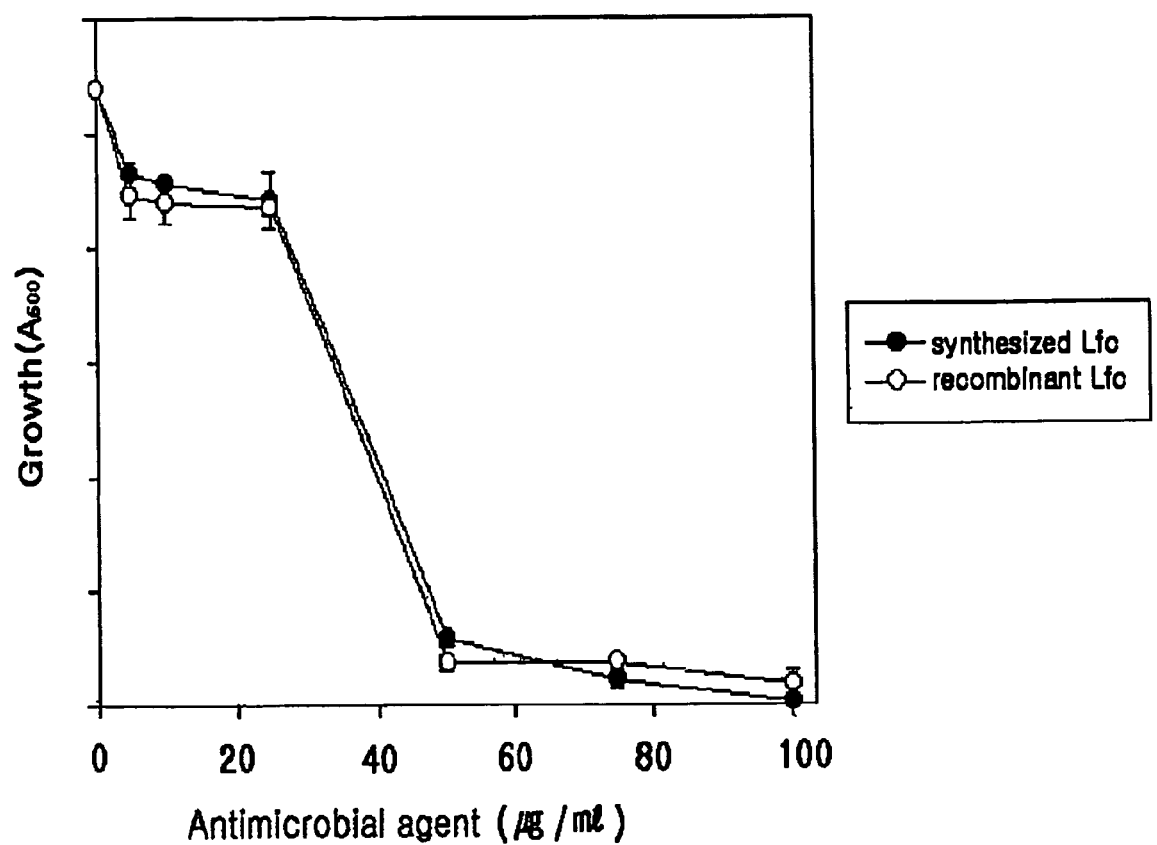
FIG. 10 is a graph showing that an effect of inhibiting the growth of E. coli of a recombinant lactoferricin according to the present invention is similar to that of the wildtype bovine lactoferricin.

After purifying the recombinant lactoferricin with glutamate and valine substituted for Gln7 and Met10, respectively, prepared in Examples 1 and 2, its biological activity was evaluated. Antimicrobial activity of the recombinant lactoferricin was measured using E. coli as a test bacterium. In particular, effect of the recombinant lactoferricin on the growth of E. coli was investigated at various concentrations. The recombinant lactoferricin expressed in *E. coli* and a chemically synthesized wildtype bovine lactoferricin as a control were added to *E. coli* cells of $10^6$/mL at various concentrations of 1 to 100 μg/mL, and the *E. coli* cells were then inoculated in a 1% bactopeptone solution and put into each well of a microtiter plate. After incubation for 24 hrs, turbidity of the medium was measured at 600 nm. The recombinant lactoferricin expressed in *E. coli* was found to inhibit the growth of *E. coli* at a concentration of over 50 μg/mL, and such an effect of the recombinant lactoferricin is identical to that of the wildtype bovine lactoferricin (see, FIG. 10).

INDUSTRIAL APPLICABILITY

As described hereinbefore, a gene encoding a mutated lactoferricin peptide having amino acid substitutions for the 7th and 10th residues of the wildtype peptide can be expressed in *E. coli* at high efficiency, and the expressed mutated lactoferricin peptide can be purified at high yield, thus making its mass production possible. In addition, the mutated lacotoferricin peptide expressed in *E. coli* has biological activities, such as antimicrobial activity, thus allowing its use instead of the conventional antibiotics, and as an immunomodulator and an antiviral agent.

The invention claimed is:

1. A mutated lactoferricin peptide having the amino acid sequence set forth in SEQ ID NO: 3, wherein glutamate and valine substituted for Gln7 and Met10, respectively, of the wildtype bovine lactoferricin, wherein said mutated lactoferricin retains the antimicrobial activity of wild type lactoferrin.

2. An isolated gene encoding the mutated lactoferricin peptide of claim 1, wherein said gene comprises the nucleotide sequence set forth in SEQ ID NO: 2.

3. A recombinant expression vector pET-MLnX comprising a fusion gene containing the gene of claim 2 and a magainin gene, wherein the fusion gene comprises the nucleotide sequence set forth in SEQ ID NO: 4.

4. The recombinant expression vector pET-MLnX as set forth in claim 3, wherein the recombinant expression vector is selected from the group consisting of a pET-ML1X plasmid, a pET-ML2X plasmid, a pET-ML3X plasmid and a pET-ML4X plasmid, which comprise tandem repeats of 1, 2, 3 and 4 copies of the fusion gene, respectively.

5. An *E. coli* cell (BL21(DE3)[pET-MLnX]) transformed with the recombinant expression vector pET-MLnX of claim 3 or 4.

6. A method of producing the lactoferricin peptide of claim 1, comprising the steps of:
   culturing the *E. coli* cell (BL21(DE3)[pET-MLnX]) of claim 5;
   treating the resulting incubated *E. coli* cell with IPTG;
   harvesting the culture; and
   recovering the peptide from the culture.

* * * * *

SEQUENCE LISTING

```
<160> NUMBER OF SEQ ID NOS: 22

<210> SEQ ID NO 1
<211> LENGTH: 25
<212> TYPE: PRT
<213> ORGANISM: lactoferricin amino acid of bovine

<400> SEQUENCE: 1

Phe Lys Cys Arg Arg Trp Gln Trp Arg Met Lys Lys Leu Gly Ala Pro
1               5                  10                  15

Ser Ile Thr Cys Val Arg Arg Ala Phe
            20                  25

<210> SEQ ID NO 2
<211> LENGTH: 75
<212> TYPE: DNA
<213> ORGANISM: Artificial Sequence
<220> FEATURE:
<223> OTHER INFORMATION: lactoferricin gene derived from bovine
      substituted 7 and 10 amino acid
<220> FEATURE:
<221> NAME/KEY: CDS
<222> LOCATION: (1)..(75)

<400> SEQUENCE: 2 ttc aaa tgc cgt cgt tgg gaa tgg cgt gtt aaa aaa ctg ggt gct ccg      48
Phe Lys Cys Arg Arg Trp Glu Trp Arg Val Lys Lys Leu Gly Ala Pro
1               5                  10                  15 tcc atc acc tgc gtt cgt cgt gct ttc                                  75
Ser Ile Thr Cys Val Arg Arg Ala Phe
            20                  25

<210> SEQ ID NO 3
<211> LENGTH: 25
<212> TYPE: PRT
<213> ORGANISM: Artificial Sequence
<220> FEATURE:
<223> OTHER INFORMATION: lactoferricin gene derived from bovine
      substituted 7 and 10 amino acid

<400> SEQUENCE: 3

Phe Lys Cys Arg Arg Trp Glu Trp Arg Val Lys Lys Leu Gly Ala Pro
1               5                  10                  15

Ser Ile Thr Cys Val Arg Arg Ala Phe
            20                  25

<210> SEQ ID NO 4
<211> LENGTH: 150
<212> TYPE: DNA
<213> ORGANISM: Artificial Sequence
<220> FEATURE:
```

```
<223> OTHER INFORMATION: Chemically synthesized fusion gene containing a
      bovine lactoferricin
      gene and a magainin gene
<220> FEATURE:
<221> NAME/KEY: CDS
<222> LOCATION: (1)..(150)

<400> SEQUENCE: 4 ccc ctg tgc gac gct gaa gct gtt ggt ccg gaa gct ttc gct gac gaa      48
Pro Leu Cys Asp Ala Glu Ala Val Gly Pro Glu Ala Phe Ala Asp Glu
1               5                   10                  15 gac ctg gac gaa tgc ccc ctg atg ttc aaa tgc cgt cgt tgg gaa tgg      96
Asp Leu Asp Glu Cys Pro Leu Met Phe Lys Cys Arg Arg Trp Glu Trp
            20                  25                  30 cgt gtt aaa aaa ctg ggt gct ccg tcc atc acc tgc gtt cgt cgt gct     144
Arg Val Lys Lys Leu Gly Ala Pro Ser Ile Thr Cys Val Arg Arg Ala
        35                  40                  45 ttc atg                                                             150
Phe Met
    50

<210> SEQ ID NO 5
<211> LENGTH: 50
<212> TYPE: PRT
<213> ORGANISM: Artificial Sequence
<220> FEATURE:
<223> OTHER INFORMATION: Chemically synthesized fusion peptide of SEQ ID
      NO: 4

<400> SEQUENCE: 5

Pro Leu Cys Asp Ala Glu Ala Val Gly Pro Glu Ala Phe Ala Asp Glu
1               5                   10                  15

Asp Leu Asp Glu Cys Pro Leu Met Phe Lys Cys Arg Arg Trp Glu Trp
            20                  25                  30

Arg Val Lys Lys Leu Gly Ala Pro Ser Ile Thr Cys Val Arg Arg Ala
        35                  40                  45

Phe Met
    50

<210> SEQ ID NO 6
<211> LENGTH: 55
<212> TYPE: DNA
<213> ORGANISM: Artificial Sequence
<220> FEATURE:
<223> OTHER INFORMATION: chemically synthesized oligonucleotide mag-F

<400> SEQUENCE: 6
gatcgacgct gaagctgttg gtccggaagc tttcgctgac gaagacctgg acgaa         55

<210> SEQ ID NO 7
<211> LENGTH: 55
<212> TYPE: DNA
<213> ORGANISM: Artificial Sequence
<220> FEATURE:
<223> OTHER INFORMATION: chemically synthesized oligonucleotide mag-R

<400> SEQUENCE: 7
agctttcgtc caggtcttcg tcagcgaaag cttccggacc aacagcttca gcgtc         55

<210> SEQ ID NO 8
<211> LENGTH: 87
<212> TYPE: DNA
<213> ORGANISM: Artificial Sequence
<220> FEATURE:
<223> OTHER INFORMATION: chemically synthesized oligonucleotide Lfc-F
```

<400> SEQUENCE: 8
cccctgatgt tcaaatgccg tcgttgggaa tggcgtgtta aaaaactggg tgctccgtcc    60
atcacctgcg ttcgtcgtgc tttcatg                                       87

<210> SEQ ID NO 9
<211> LENGTH: 87
<212> TYPE: DNA
<213> ORGANISM: Artificial Sequence
<220> FEATURE:
<223> OTHER INFORMATION: chemically synthesized oligonucleotide Lfc-R

<400> SEQUENCE: 9
ggggcatgaa agcacgacga acgcaggtga tggacggagc acccagtttt ttaacacgcc    60
attcccaacg acggcatttg aacatca                                       87

<210> SEQ ID NO 10
<211> LENGTH: 45
<212> TYPE: DNA
<213> ORGANISM: Artificial Sequence
<220> FEATURE:
<223> OTHER INFORMATION: chemically synthesized PCR primer BS-F

<400> SEQUENCE: 10
agacccgggg ccgtcttcgc atccggatcc ccgggtaccg agctc                   45

<210> SEQ ID NO 11
<211> LENGTH: 45
<212> TYPE: DNA
<213> ORGANISM: Artificial Sequence
<220> FEATURE:
<223> OTHER INFORMATION: chemically synthesized PCR primer BS-R

<400> SEQUENCE: 11
ggatgcgaag acggccccgg gtcttctaga gtcgacctgc aggca                   45

<210> SEQ ID NO 12
<211> LENGTH: 40
<212> TYPE: DNA
<213> ORGANISM: Artificial Sequence
<220> FEATURE:
<223> OTHER INFORMATION: chemically synthesized PCR primer Mag-1

<400> SEQUENCE: 12
aaagaagacg gccctgtgc gacgctgaag ctgttggtcc                          40

<210> SEQ ID NO 13
<211> LENGTH: 34
<212> TYPE: DNA
<213> ORGANISM: Artificial Sequence
<220> FEATURE:
<223> OTHER INFORMATION: chemically synthesized PCR primer Mag-2

<400> SEQUENCE: 13
catcaggggg cattcgtcca ggtcttcgtc agcg                               34

<210> SEQ ID NO 14
<211> LENGTH: 32
<212> TYPE: DNA
<213> ORGANISM: Artificial Sequence
<220> FEATURE:
<223> OTHER INFORMATION: chemically synthesized PCR primer Lfc-3

<400> SEQUENCE: 14

```
ctggacgaat gccccctgat gttcaaatgc cg                                    32
```

<210> SEQ ID NO 15
<211> LENGTH: 44
<212> TYPE: DNA
<213> ORGANISM: Artificial Sequence
<220> FEATURE:
<223> OTHER INFORMATION: chemically synthesized PCR primer Lfc-4

<400> SEQUENCE: 15

```
ctagaagacc cggggcatga agcacgacg aacgcaggtg atgg                        44
```

<210> SEQ ID NO 16
<211> LENGTH: 23
<212> TYPE: DNA
<213> ORGANISM: Artificial Sequence
<220> FEATURE:
<223> OTHER INFORMATION: chemically synthesized M13 forward primer

<400> SEQUENCE: 16

```
cccagtcacg acgttgtaaa acg                                              23
```

<210> SEQ ID NO 17
<211> LENGTH: 23
<212> TYPE: DNA
<213> ORGANISM: Artificial Sequence
<220> FEATURE:
<223> OTHER INFORMATION: chemically synthesized M13 reverse primer

<400> SEQUENCE: 17

```
agcggataac aatttcacac agg                                              23
```

<210> SEQ ID NO 18
<211> LENGTH: 23
<212> TYPE: DNA
<213> ORGANISM: Artificial Sequence
<220> FEATURE:
<223> OTHER INFORMATION: chemically synthesized primer pUBS-R

<400> SEQUENCE: 18

```
ctgcaggtcg actctgaaga ccc                                              23
```

<210> SEQ ID NO 19
<211> LENGTH: 56
<212> TYPE: DNA
<213> ORGANISM: Artificial Sequence
<220> FEATURE:
<223> OTHER INFORMATION: chemically synthesized BbsI multiple cloning
     site

<400> SEQUENCE: 19

```
cccggggatc cggatgcgaa gacggccccg ggtcttctag agtcgacctg caggca          56
```

<210> SEQ ID NO 20
<211> LENGTH: 176
<212> TYPE: DNA
<213> ORGANISM: Bovine
<220> FEATURE:
<221> NAME/KEY: CDS
<222> LOCATION: (12)..(161)

<400> SEQUENCE: 20

```
aaagaagacg g ccc ctg tgc gac gct gaa gct gtt ggt ccg gaa gct ttc       50
             Pro Leu Cys Asp Ala Glu Ala Val Gly Pro Glu Ala Phe
             1               5                   10 gct gac gaa gac ctg gac gaa tgc ccc ctg atg ttc aaa tgc cgt cgt        98
```

-continued

```
Ala Asp Glu Asp Leu Asp Glu Cys Pro Leu Met Phe Lys Cys Arg Arg
    15              20                  25 tgg gaa tgg cgt gtt aaa aaa ctg ggt gct ccg tcc atc acc tgc gtt        146
Trp Glu Trp Arg Val Lys Lys Leu Gly Ala Pro Ser Ile Thr Cys Val
30              35                  40                  45 cgt cgt gct ttc atg ccccgggtct tctag                                   176
Arg Arg Ala Phe Met
                50
```

<210> SEQ ID NO 21
<211> LENGTH: 49
<212> TYPE: DNA
<213> ORGANISM: Artificial Sequence
<220> FEATURE:
<223> OTHER INFORMATION: chemically synthesized oligonucleotide to
      prepare the recombinant expression vector pET-MLnX expressing
      lactoferricin

<400> SEQUENCE: 21
gggatccgga tgcgaagacg gccccgggtc ttctagagtc gacctgcgg                  49

<210> SEQ ID NO 22
<211> LENGTH: 49
<212> TYPE: DNA
<213> ORGANISM: Artificial Sequence
<220> FEATURE:
<223> OTHER INFORMATION: chemically synthesized oligonucleotide to
      prepare the recombinant expression vector pET-MLnX expressing
      lactoferricin

<400> SEQUENCE: 22
ccctaggcct acgcttctgc cggggcccag aagatctcag ctggacgcc                  49